United States Patent
Rahimipour (10) Patent No.: US 9,504,759 B2
(45) Date of Patent: Nov. 29, 2016

(54) SURFACE MODIFIED PROTEINACEOUS SPHERICAL PARTICLES AND USES THEREOF

(75) Inventor: Shai Rahimipour, Rehovot (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 0 days.

(21) Appl. No.: 14/237,890

(22) PCT Filed: Aug. 8, 2012

(86) PCT No.: PCT/IB2012/054037
§ 371 (c)(1),
(2), (4) Date: Mar. 31, 2014

(87) PCT Pub. No.: WO2013/021353
PCT Pub. Date: Feb. 14, 2013

(65) Prior Publication Data
US 2014/0205668 A1 Jul. 24, 2014

Related U.S. Application Data

(60) Provisional application No. 61/573,033, filed on Aug. 11, 2011.

(51) Int. Cl.
*A61K 47/48* (2006.01)
*C07K 7/64* (2006.01)
*A61K 49/18* (2006.01)

(52) U.S. Cl.
CPC ... *A61K 47/48876* (2013.01); *A61K 47/48869* (2013.01); *A61K 49/1866* (2013.01); *C07K 7/64* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 7,288,523 | B2 | 10/2007 | Nordstedt et al. |
| 7,658,917 | B2 | 2/2010 | Findeis et al. |
| 2004/0258762 | A1 | 12/2004 | Boppart et al. |
| 2006/0275257 | A1* | 12/2006 | Nissen ............ A61K 9/0019 424/85.1 |
| 2007/0010435 | A1 | 1/2007 | Frangione et al. |
| 2011/0064821 | A1 | 3/2011 | Catchpole et al. |
| 2014/0205668 | A1* | 7/2014 | Rahimipour ..... A61K 47/48869 424/489 |

FOREIGN PATENT DOCUMENTS

| | | |
|---|---|---|
| EP | 2258398 | 12/2010 |
| JP | 2002241302 | 8/2002 |
| JP | 2002265382 | 9/2002 |
| WO | 9418954 | 9/1994 |
| WO | 9721728 | 6/1997 |
| WO | WO 2004005685 | * 6/2004 |
| WO | 2005023096 | 3/2005 |
| WO | 2005058941 | 6/2005 |
| WO | 2006026184 | 3/2006 |
| WO | 2007015107 | 2/2007 |
| WO | 2007047967 | 4/2007 |
| WO | 2009155538 | 12/2009 |
| WO | 2011053901 | 5/2011 |

OTHER PUBLICATIONS

Bastus et al; Gold nanoparticles for selective and remote hearing of beta-amyloid protein aggregates; Materials Science and Engeering C, vol. 27, No. 5-8, Aug. 8, 2007.
Olmedo et al; How Changes in the Sequence of the Peptide CLPFFD-NH 2 Can Modify the Conjugation and Stability of Gold Nanoparticles and their Affinity for (beta)-Amyloid Fibrils, Bioconjugate Chemistry, vol. 19, No, 6, Jun. 1, 2008, pp. 1154-1163.
A. Majzik et al; Functionalization of gold nanoparticles with amino acid, beta-amyloid pepties and fragment, Colloids and Surfaces, B. Biointerfaces, vol. 81, No. 1, Nov. 1, 2010, pp. 235-241.
M. El Mouedden et al; Development of a specific ELISA for the quantitative study of amino-terminally truncated beta-amyloid peptides; Journal of Neuroscience Methods, vol. 145, No. 1-2, Jun. 30, 2005, pp. 97-105.
B. Neddenriep et al; Short Peptides as Inhibitors of Amyloid Aggregation; The Open Biotechnology Journal, vol. 5, No. 1, Dec. 23, 2011, pp. 39-46.
M. Richman et al; Effective Targeting of Aβ to Macrophages by Sonochemically Prepared Surface-Modified Protein Microspheres; Acs Publications, American Chemical Society, Biomacromolecules 2013, vol. 14, pp. 110-116.
M. Richman et al; Surface-Modified Protein Microspheres Capture Amyloid-b and Inhibit its Aggregation and Toxicity Chemistry European Journal 2011, 17, pp. 11171-11177.
I.W. Hamley et al; Nematic and columnar ordering of a PEG-peptide conjugate in aqueous solution; Chemistry; 2008; 14(36)—abstract.
PCT International Search Report for PCT/IB2012/054037, mailed Jan. 1, 2013.

* cited by examiner

*Primary Examiner* — Maury Audet
(74) *Attorney, Agent, or Firm* — A.C. Entis-IP Ltd.

(57) ABSTRACT

An aspect of embodiments of the invention relates to surface modified proteinaceous spherical particles (SMOP). SMOPs according to an embodiment of the invention may comprise a protein layer and an amyloid-binding moiety bound to the protein. In an embodiment, the protein layer is spherical in shape and comprises proteins linked to each other by disulfide bonds. It is suggested that SMOPs are effective in preventing formation of amyloid and aggregation of Aβ when administered to a patient in need thereof.

1 Claim, 3 Drawing Sheets

SURFACE MODIFIED PROTEINACEOUS SPHERICAL PARTICLES AND USES THEREOF

RELATED APPLICATIONS

The present application is a U.S. National Phase of PCT Application No. PCT/IB2012/054037, filed on Aug. 8, 2012, which claims the benefit under 35 U.S.C. §119(e) of U.S. Provisional 61/573,033 filed on 11 Aug. 2011, the disclosure of which is incorporated herein by reference.

RELATED APPLICATIONS

The present application claims the benefit under 35 U.S.C. 119(e) of U.S. Provisional Application 61/573,033 filed on 11 Aug. 2011, the disclosure of which is incorporated herein by reference.

TECHNICAL FIELD

Embodiments of the invention relate to surface modified proteinaceous particles, methods of their manufacture, and uses of the particles.

BACKGROUND

One of the main causes of dementia in elderly patients is Alzheimer's Disease (AD). AD is caused by degeneration in various parts of the brain attributed to loss of brain neurons and synapses. Amyloid fibrils and plaques are commonly found in brains of patients afflicted by AD, and it has been suggested that formation and growth of amyloid plaques are one of the main causes of AD.

Amyloid plaques are formed primarily by the aggregation and accumulation of naturally occurring proteins. One protein, which causes amyloid formation, is termed Amyloid Beta, also known as Beta Amyloid (Aβ). Aβ is a peptide composed of between 40 and 43 amino acids and it exists in humans in both soluble and insoluble forms. In its soluble form, it circulates in plasma and in brain interstitial and cerebrospinal fluids. In its insoluble form, Aβ forms aggregates comprising amyloid fibrils which can form disease-causing amyloid plaques.

In addition to Aβ, other proteins such as amylin, alpha-synuclein, Huntingtin and beta-2 microglobulin have been indicated as causes for amyloid formation.

In addition to AD, other diseases have been associated with accumulation of amyloid plaques including Lewy body dementia, cerebral amyloid angiopathy and inclusion body myositis.

SUMMARY

An aspect of embodiments of the invention relates to surface modified proteinaceous spherical particles (SMOP). SMOPs according to an embodiment of the invention may comprise a protein layer and an amyloid-binding moiety bound to the protein. In an embodiment, the protein layer is spherical in shape and comprises proteins linked to each other by disulfide bonds.

It is suggested that SMOPs are effective in preventing formation of amyloid and aggregation of Aβ when administered to a patient in need thereof. Without being bound by theory, the amyloid-binding moiety on the surface of the SMOP binds to an amyloid forming protein, such as Aβ (both soluble and aggregated forms) to form an SMOP-Aβ complex. The SMOP-Aβ complex prevents Aβ aggregation and toxicity. In addition, the SMOP-Aβ is then recognized by cells (including macrophages) which perform phagocytosis, thereby eliminating the SMOP-Aβ complex. As a result, the systemic concentration of Aβ and/or Aβ plaques present in the patient is reduced.

In addition, SMOPs may be used for diagnostics in the detection of amyloid plaques and/or Aβ-containing plaques present in the patient. SMOPs may be manufactured to further comprise a contrasting agent. Upon administration to a patient, SMOPs may migrate to areas of the patient's body comprising high concentrations of amyloid and/or Aβ plaques. SMOPs comprising a contrasting agent may then be detected using diagnostic methods to analyze for accumulations of SMOPs which may indicate high concentrations of Aβ and/or Aβ plaques in the patient.

Additional aspects of embodiments of the invention relate to methods of manufacture of SMOPs using sonication. In an embodiment of the invention, a protein having a thiol group, for example, a cysteine residue, is combined with a biologically active agent having a thiol group to form a mixture, and the mixture is sonicated to form SMOPs.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION

As will be described in the following examples, it has been found that SMOPs comprising an Aβ binding moiety bound to a protein, have been effective in reducing concentration of Aβ and preventing aggregation and toxicity of Aβ SMOPs according to embodiments of the invention may be used for treatment and diagnosis of Aβ-mediated diseases.

EXAMPLE 1A

Synthesis of Modified Protein Particles Using Sonication

SMOPs modified with a peptide having the sequence KLVFFC-NH2 (SEQ ID NO 3) motif were prepared. KLVFF (SEQ ID NO 1) is a short peptide representing residues 16-20 in native Aβ and has been shown to bind homologous Aβ and inhibit its aggregation.

Figure 1:
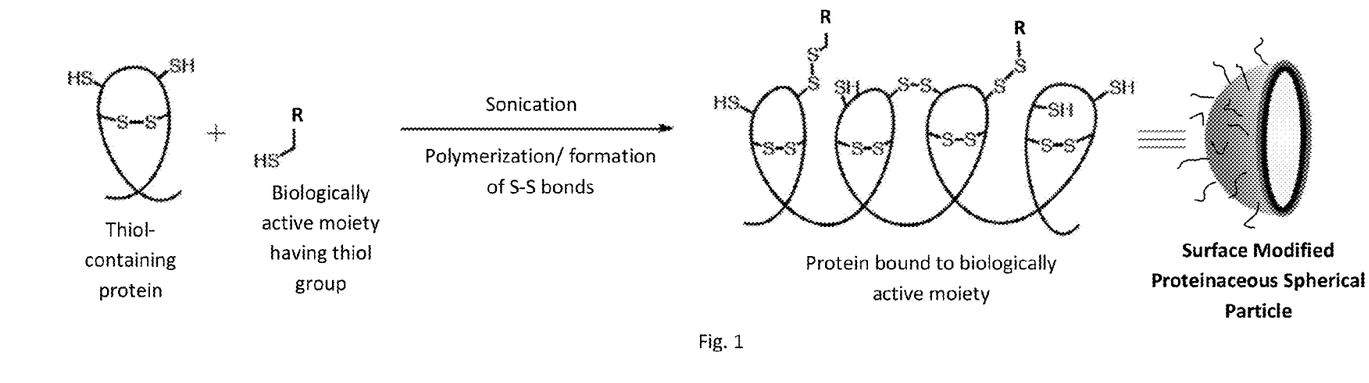
FIG. 1 shows a schematic representation of a synthesis of an SMOP, in accordance with an embodiment of the invention.

In a one-step process, peptides having a sequence KLVFFC-NH2 (SEQ ID NO 3) or its analogs were covalently attached via disulfide bonds to protein molecules, and the protein molecules' tertiary structure re-organized via breaking and formation of disulfide bonds to form SMOP particles. A general depiction of this process is shown in FIG. 1.

In order to attach the Aβ binding element KLVFF (SEQ ID NO 1) to protein molecules which would form spherical protein particles, an amino acid having a thiol group, cysteine, was introduced on the C-terminal of the KLVFF (SEQ ID NO 1) peptide. Peptides having the sequence KLVFFC-NH2 (SEQ ID NO 3) were synthesized using solid phase peptide synthesis. A Rink amide MBHA (paramethylbenzhydrylamine) resin was used, with FMOC (Fluorenylmethyloxycarbonyl) protection. Coupling was carried out in N-methyl-2-pyrrolidone (NMP), and 2-(1H-benzotriazol-1-yl)-1,1,3,3-tetramethyluronium hexafluorophosphate (HBTU) was used as the coupling agent. The peptides were cleaved from resin and deprotected by a mixture of trifluoroacetic acid (TFA): Triisopropylsilane: H2O (95 :2.5:2.5) and purified to homogeneity by RP-HPLC (reversed phase high-performance liquid chromatography). The pure peptides were analyzed by mass spectrometry using MALDI-TOF/TOF (Matrix-assisted laser desorption/ionization, time of flight) or ESI (electrospray ionization) mass spectrometer.

SMOPs were prepared sonochemically by sonicating a reaction mixture of peptide, solvent and protein. In an embodiment of the invention, a solution of bovine serum albumin (BSA) in an amount of 1.5 milligrams (mg) in 30 milliliters (ml) of double-distilled water was combined with canola oil (20 ml) in a cylindrical reaction vessel. KLVFFC-NH2 (SEQ ID NO 3) was added to the BSA solution in a molar ratio of BSA:peptide 1:500. The tip of a high-intensity ultrasonic probe was then placed at the aqueous-organic interface and the mixture was irradiated at an acoustic power of 150 Watts per square centimeter (W/cm2) of surface area of probe at 20 kilohertz for three minutes while the reaction vessel was cooled in an ice-water bath. After synthesis, the reaction mixture was left at 4° C. (Celsius) for 24-36 hours, and SMOP phase was separated from the unreacted BSA. The SMOPs were washed by centrifuging twice with 25 ml of distilled water at 800 revolutions per minute.

In alternative embodiments of the invention, other proteins can be used, including human serum albumin or transferrin. Antibodies may also be used in place of proteins. SMOPs may be formed of any proteins or peptides having amino acids comprising thiol groups, such as cysteine or homocysteine. In addition, SMOP protein layers may be formed from polymers and biopolymers, optionally having thiol groups. These proteins or peptides may form disulfide bonds to form spherical protein or peptide structures, capable of chemically bonding to Aβ binding elements.

Without being bound by theory, it is suggested that syntheses of SMOP described herein may be explained as follows. Sonication of reaction mixtures comprising an oil, a thiol containing protein, and an amyloid binding moiety comprising a thiol agent, breaks and reforms disulfide bonds between protein molecules and between proteins and amyloid binding moieties. Oil-filled particles having a spherical shape and having a protein coating are formed, and the amyloid binding moieties are bound to external surfaces on the outside of the protein coatings by a thiol exchange reaction.

EXAMPLE 1B

Synthesis of Labeled SMOPs

In order to estimate amount of peptide bound on each SMOP, labeled SMOPs were synthesized. The procedure used in Example 1A was followed with the exception that the peptide used, KLVFFC-NH2(SEQ ID NO 3), was labeled at its N-terminus by reaction with 4-nitrobenzo-1, 2,5-oxadiazole (NBD) chloride after solid state synthesis, before detachment from the resin. The labeled peptide formed, designated NBD-KLVFFC-NH2 was then sonicated with BSA as in Example 1A to form NBD labeled SMOPs.

In addition, SMOPs encapsulated with Nile red were synthesized by following the procedure in Example 1A, with the addition of 5 mg Nile red to the 20 ml canola oil used in the reaction mixture. The Nile red-encapsulated SMOPs were then characterized using various methods, including fluorescent and electron microscopy.

EXAMPLE 1C

Synthesis of Additional SMOPs

SMOPs were formed with a "scrambled" peptide having the same amino acids as KLVFF (SEQ ID NO 1) in a different sequence, FVKLF. The method for preparation used was similar to that used in Example 1A with the exception of using FVKLFC-NH2(SEQ ID NO 4) as a starting material. These SMOPs function as a comparator in in vitro studies to KLVFF (SEQ ID NO 1) -containing SMOPs.

In example 1A, molar ratio of protein to peptide starting material was approximately 1:500. Other SMOPs were prepared using a molar ratio of starting materials ranging from 1:100 to 1:1000.

SMOPs comprising polyethylene glycol (PEG) were also prepared using the general method as in Example 1A but with the addition of PEG. To prepare PEG-SMOPs 0.6 mg of mercapto-polyethylene glycol monomethyl ether (molecular weight of about 5000 grams/mole (g/mole)) was mixed in the BSA (1.5 mg, 0.023 micromole (μmol)) and KLVFFC-NH2 (SEQ ID NO 3) (8.6 mg, 11.4 μmol) solutions and combined with a layer of canola oil. The mixture was then subjected to the sonication as described in Example 1A.

EXAMPLE 1D

Characterization of SMOP

The KLVFF (SEQ ID NO 1) -comprising SMOPs were characterized by optical and scanning electron microscopy (SEM), dynamic light scattering (DLS) and fluorescent microscopy. The shape and morphology of the SMOPs were characterized by optical-fluorescence microscopy (ApoTome Axiolmager.z1 microscope, Zeiss, Germany), scanning electron microscopy (SEM, FEI Quanta™ 200 FEG, Hillsboro, Oregon) and confocal microscopy (Leica-SPE microscope, Mannheim, Germany). For the SEM analyses, a sample (10 microliters (μl)) of SMOP was spotted onto a glass wafer, followed by drying and gold sputtering. The samples were then analyzed by SEM. The size and the size of distribution of the SMOPs were determined by Coulter Laser Diffraction (Coulter LS 100 Q Laser Sizer, Beckman Coulter, Miami, FLA, USA).

The optical and SEM images show the SMOPs to be spherical with relatively smooth surfaces. The DLS measurements demonstrated that the KLVFF(SEQ ID NO 1)-modified SMOPs have an average size of about 1.5 micrometer (μm) with a narrow size distribution. Using fluorescent microscopy for detection of NBD in NBD-labeled KLVFF (SEQ ID NO 1)-modified SMOPs showed that KLVFF (SEQ ID NO 1) peptide was confined to the outer surface of the SMOPs. Fluorescent microscopy analysis of SMOPs encapsulating oil-soluble Nile red confirmed that the SMOPs were filled with an organic oil-based core which was surrounded by a protein shell. This indicates that SMOPs can be used as encapsulation agents, in particular of oil-soluble reagents, for treatment and/or diagnosis.

The amount of KLVFF (SEQ ID NO 1) peptide on SMOP's surface was estimated using UV spectroscopy of NBD-labeled SMOPs, at a wavelength of 465 nanometers (nm). The number of SMOPs per volume was calculated using flow-cytometry analysis, (fluorescence-activated cell sorting, (FACS)). The molar ratio of starting materials varied from 1:100 to 1:1000. The amount (number of SMOPs per unit volume), sizes and amounts of peptide present in SMOPs prepared according to procedures described above are summarized in Table 1. "ND" indicates that value was not determined.

TABLE 1

Analysis of various BSA-comprising SMOPs

| Peptide | Molar ratio (Protein:Peptide) | Diameter (micrometers) | Amount of SMOPs (millions per ml) | KLVFF (SEQ ID NO 1) amount (nanomoles/ml) |
|---|---|---|---|---|
| KLVFF (SEQ ID NO 1) | 1:1000 | 1.49 ± 1.36 | 160.0 | 128 |
| KLVFF (SEQ ID NO 1) | 1:500 | 1.73 ± 1.37 | 208 | 80 |
| KLVFF (SEQ ID NO 1) | 1:100 | ND | 260 | 38 |
| FVKLF | 1:1000 | 2.40 ± 1.33 | 260 | ND |
| FVKLF | 1:500 | 2.25 ± 1.30 | 320 | ND |

As seen in table 1, a linear correlation was observed between the amount of NBD-labeled KLVFF (SEQ ID NO 1) on the surface of SMOP and the amount of peptide used as a starting material in each preparation.

Without being bound by theory, it is suggested that when proteins comprising thiol groups are sonicated with peptides comprising thiol groups in the presence of oil, disulfide bonds are formed between protein molecules and due to hydrophobic/hydrophilic interactions between proteins and oil, the proteins tend to form spheres which encapsulate the oil, and tend to present the peptides on their outer surfaces.

EXAMPLE 1E

Binding of Aβ by SMOP

Binding of KLVFF (SEQ ID NO 1)-modified SMOP to Aβ was assessed using a fluorescent modified Aβ known as FITC-Aβ40 (fluorescein isothiocyanate) in a direct in vitro assay. In order to confirm that the conjugated KLVFF (SEQ ID NO 1) fragments on SMOPs preserved their recognition capability to bind full length Aβ following the sonochemical process and SMOP generation, KLVFF (SEQ ID NO 1)-modified SMOPs were incubated with soluble FITC-Aβ40 (25 μ, 0.5 nanomolar, nM) in PBS at 37° C. for different periods under constant agitation (750 revolutions per minute (rpm)). At each time point, samples were diluted with cold PBS and the microspheres were washed twice with cold PBS. Ten thousand particles were then analyzed immediately by FACS.

In addition, an indirect assay (ThT [Thioflavin T] assay) was performed as follows. In the ThT assay, the ThT dye binds to amyloid plaque formations and displays enhanced fluorescence. The fluorescence is measured and correlated to presence of amyloid plaque formations. Agents which bind and inhibit amyloid plaque formation decrease fluorescence of ThT. The inhibitory activity of KLVFF (SEQ ID NO 1)-modified SMOPs on Aβ40 aggregation was determined in black 96-well flat-bottom plates by incubating fresh monomerized (non-aggregated) solutions of Aβ40 (33 micromolar (μM), 15 μl) with different preparations of the SMOPs (25 μl, Table 1) in PBS. PBS was added to reach a volume of 50 μl, giving a final concentration of 10 μM for Aβ40. The inhibitory activity of the KLVFF (SEQ ID NO 1)-modified SMOPs was compared to that of soluble KLVFF-NH2(SEQ ID NO 2) peptide alone or to the SMOPs with the scrambled peptide, FVKLFC-NH2(SEQ ID NO 4). The plates were sealed with aluminum foil and incubated while shaking at 750 rpm at 37° C. for 72 hours to induce aggregation. Following the incubation, a solution of ThT (24 μM, 150 μl) in glycine buffer (50 millimolar (mM), pH 8.5) was added to each well and the fluorescence of amyloid-bound ThT was immediately measured using a plate reader (Infinite M200, Tecan, Switzerland) at excitation and emission wavelengths of 430 and 492 nm, respectively. The ThT solution was freshly prepared by diluting a ThT stock solution (1 mM, in water) with glycine buffer (50 mM, pH 8.5). Experiments were performed in quadruplicate.

As controls, proteinaceous SMOP without surface modification (prepared as in example 1A, without the addition of a KLVFF (SEQ ID NO 1) peptide) (naked BSA spheres) were prepared. FVKLF-modified SMOP was also prepared as a control, as in Example 1C.

Both fluorescent microscopy and FACS analysis showed intense fluorescent signals on the KLVFF-modified SMOPs even after extensive washing steps, indicative of strong affinity of FITC-Aβ40 to the KLVFF (SEQ ID NO 1)-modified SMOPs. In contrast, significantly lower amount of FITC-Aβ40 was accumulated on the surface of the naked BSA spheres and the FVKLF-modified SMOPs. These results confirm that the selective interaction of KLVFF (SEQ ID NO 1)-modified SMOP with Aβ40 is mediated through the KLVFF (SEQ ID NO 1) binding site and that KLVFF (SEQ ID NO 1)-modified SMOP may potentially be used to bind Aβ.

EXAMPLE 1F

Comparison of Affinity of KLVFF-Modified SMOP and KLVFF to Aβ

The selectivity and relative affinity of the interaction between KLVFF (SEQ ID NO 1)-modified SMOP and Aβ40 were further determined by probing the impact of soluble KLVFF-NH2 (not bound to SMOPs) on the binding of FITC-Aβ40 to KLVFF (SEQ ID NO 1)-modified SMOP, having a 1:500 ratio of BSA to KLVFF(SEQ ID NO 1). FACS analysis revealed that a large excess of soluble KLVFF-NH2 (SEQ ID NO 2) (×50mole excess) used as the competitor only slightly reduced (P<0.001) the binding between FITC-Aβ40 and KLVFF (SEQ ID NO 1)-modified SMOP, implying a significantly higher affinity of FITC-Aβ40 for the KLVFF-modified SMOP than for the free KLVFF-NH2 (SEQ ID NO 2) and/or the high capacity of the KLVFF (SEQ ID NO 1)-modified SMOP to bind Aβ40.

EXAMPLE 1G

Inhibition of Aβ Aggregation by SMOP

To evaluate the inhibitory effect of KLVFF (SEQ ID NO 1)-modified SMOPs on Aβ aggregation and kinetics, soluble Aβ40 (0.5 nanomol, nmol) was incubated in the absence and presence of different preparations of the SMOPs. Amyloid plaque formation was then monitored by a ThT assay for three days of incubation.

Figure 2A:
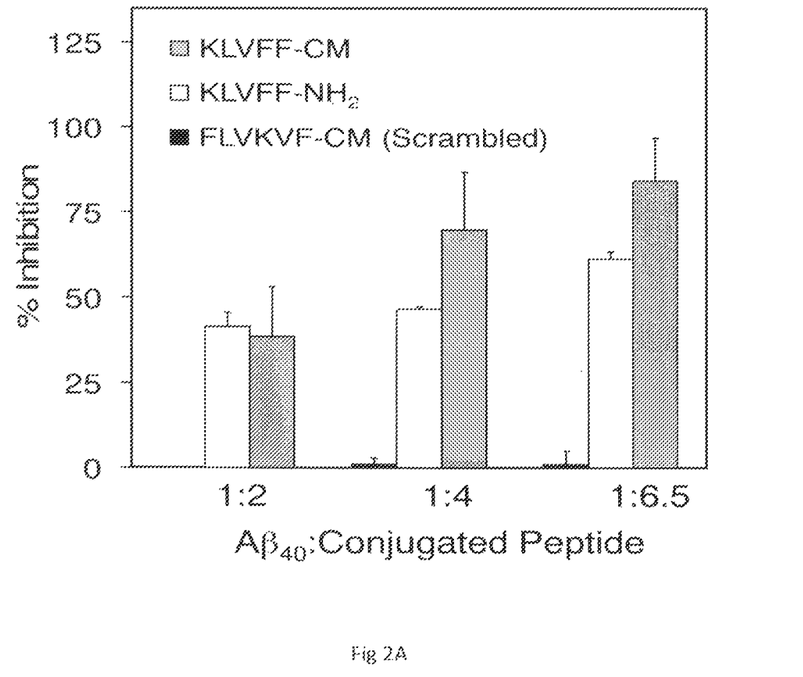
FIG. 2A shows a histogram depicting reduction of aggregation of Aβ in an in vitro model using various concentrations of SMOPs comprising Aβ binding moiety KLVFF (SEQ ID NO 1) (designated KLVFF-CM) according to embodiments of the invention as compared to soluble KLVFF-NH$_2$ (SEQ ID NO 2) peptide and scrambled peptide surface modified protein (scrambled)

KLVFF-NH2 (SEQ ID NO 2) soluble peptide was tested in ThT aggregation assay against equivalent amounts of KLVFF (SEQ ID NO 1)-modified SMOPs prepared using a BSA: KLVFF (SEQ ID NO 1) ratio of 1:500(SMOPs having equivalent amounts of KLVFF (SEQ ID NO 1) peptide) and scrambled peptide FLVKF-modified SMOPs, having equivalent amounts of peptide. Three experiments were performed in which the molar ratio of Aβ to peptide or peptide equivalent varied from 1:2 to 1:4 to 1:6.5.The KLVFF (SEQ ID NO 1)-modified SMOPs significantly decreased the aggregation of Aβ in a dose-dependent manner as shown in FIG. 2A and dramatically slowed the rate of Aβ aggregation. KLVFF-NH2 (SEQ ID NO 2) soluble peptide had an inhibitory effect on Aβ aggregation, but to a lesser extent than equivalent concentrations of KLVFF-modified SMOP. In contrast, FLKVF-modified SMOP had no or little effect on Aβ aggregation and its kinetics. These results clearly indicate that the effect of the KLVFF (SEQ ID NO 1)-modified SMOP on Aβ aggregation is sequence-specific.

The finding that KLVFF (SEQ ID NO 1)-modified SMOP had an effect on reducing amyloid aggregation is significant in that previous attempts to inhibit amyloid aggregation using particles bound to amyloid binding agents were not successful. An example of such an attempt is detailed in Kogan et al, in which gold nanoparticles conjugated to an anti-amyloidogenic peptide failed to show anti-aggregation activity, despite the strong and selective binding of the peptides to the Aβ species. The particles only succeeded in inhibiting aggregation when microwave energy was introducted to heat up the gold nanoparticles.

Transmission Electron Microscopy (TEM) analysis of the samples taken from the ThT assay demonstrated that while Aβ40 alone forms long unbranched fibrils following 72 hour incubation, addition of KLVFF (SEQ ID NO 1)-modified SMOP completely arrests the formation of fibrils. In contrast, naked BSA spheres and FLKVF-modified SMOP had no inhibitory effect on amyloid formation.

EXAMPLE 1H

Reduction of Aβ-Induced Toxicity in PC12 Cells

Having shown that the KLVFF (SEQ ID NO 1)-modified SMOP can effectively and selectively inhibit Aβ aggregation, the toxicity of SMOP was tested in PC12 cells, and the reduction of Aβ-induced toxicity in PC12 cells was tested.

PC12 cells were maintained in low-glucose Dulbecco's Modified Eagle Medium (DMEM) supplemented with 10% horse serum and 5% fetal bovine serum, 2 mM L-glutamine, 100 Units/ml penicillin and 100mg/ml streptomycin in a 5% $CO_2$ atmosphere at 37° C. PC12 cells (10,000 cells/well) were plated in 96-well tissue-culture plates in 100 μl of the medium and incubated overnight to attach cells to the plates. The medium was then replaced with 100 μl of fresh medium containing various amounts of the KLVFF (SEQ ID NO 1)-modified SMOP (5-25 μl), and the incubation was continued at 37° C. for an additional 24 hours. Cell survival was then determined by the 3-(4,5-dimethylthiazol-2-yl)-2,5-diphenyl tetrazolium bromide (MTT) assay In the MTT assay, a PBS solution of MTT (10 μl, 5 mg/ml) was added to each well after the medium was replaced with fresh medium and the cells were incubated for an additional 4 hours. The generated formazan crystals were dissolved by adding 100 μl of 50% dimethylformamide containing 20% sodium dodecyl sulfate (pH 4.7) to each well. The plates were then shaken at 37° C. overnight and the absorbance of each well was measured at 570 nm (680 nm background) using a plate reader. At the levels tested KLVFF (SEQ ID NO 1)-modified SMOP showed no signs of toxicity in PC12 cells.

In order to assess effect of KLVFF (SEQ ID NO 1)-modified SMOP on Aβ toxicity, Aβ40 (0.5 nmol) in 25 μl of PBS was aged for 48 hours in the absence or presence of either the SMOPs (25μl, 2 nmol, based on the amount of the conjugated peptide) or the soluble peptide KLVFF-NH2 (SEQ ID NO 2) (25 μl, 2 or 20 nmol). Prior to the addition of the SMOPs or soluble peptides to the cells, the extent of Aβ40 aggregation in each sample was determined by ThT assay as described above. On the day of the experiment, the medium was replaced with fresh medium (50 μl) and the aged samples (50 μ) were then diluted by a factor of two in the medium. Control wells received PBS (50 μl) only. Cells were incubated for an additional 24 hours and cell viability was then determined by the MTT assay as described above. Each experiment was performed in quadruplicate and repeated three times.

Figure 2B:
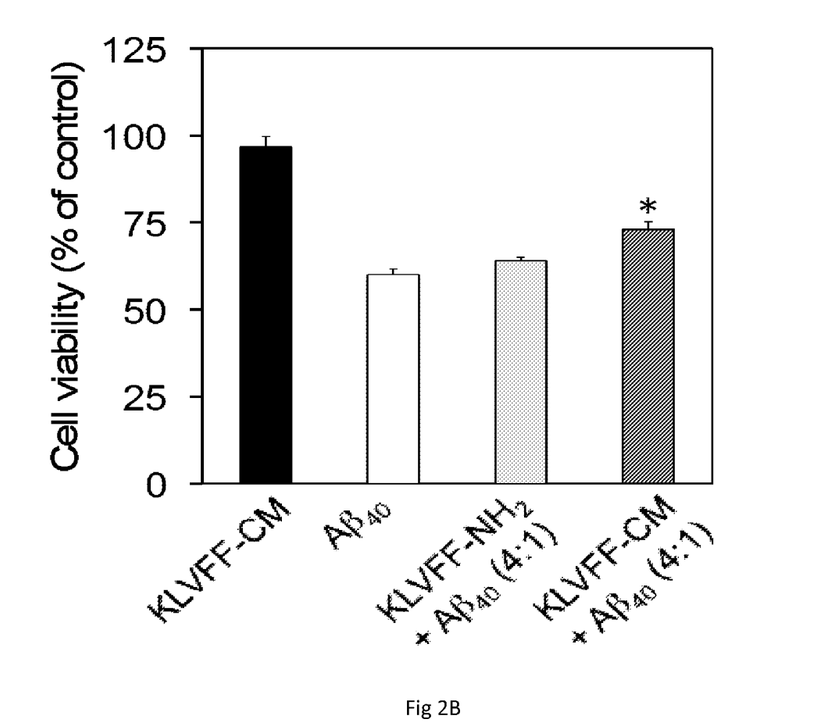
FIG. 2B shows a histogram depicting reduction of Aβ induced toxicity in a model involving rat phaeochromocytoma (PC12) cells, in which SMOPs according to embodiments of the invention (designated KLVFF-CM+Aβ40 (4:1)) were effective in reducing toxicity of Aβ to a greater extent than to equivalent amounts of soluble KLVFF-NH2 (SEQ ID NO 2)+Aβ40 (4:1)peptide.

The results are shown in FIG. 2B. Levels of cell viability (an indication of lack of toxicity) in the presence of KLVFF (SEQ ID NO 1)-modified SMOP (designated KLVFF-CM) without Aβ and Aβ without any amyloid binding agent are depicted (two leftmost bars) as comparison. KLVFF (SEQ ID NO 1)-modified SMOP (designated KLVFF-CM+Aβ40 (4:1)) significantly reduced (P<0.003) the toxicity of the aggregated Aβ as shown in FIG. 2B. In contrast, soluble KLVFF-NH2 (SEQ ID NO 2) (designated KLVFF-NH2+ Aβ40 (4:1)) exhibited little or no effect on toxicity, suggesting that the activity of the SMOP, which most likely stems from the multivalent presentation of the KLVFF (SEQ ID NO 1) peptides, is greater than the activity of soluble KLVFF (SEQ ID NO 1) on eliminating toxicity associated with amyloid aggregation.

EXAMPLE 2A

Administration of SMOP to Animals to Demonstrate Safety

SMOPs modified with KLVFF (SEQ ID NO 1) (ratio of BSA:KLVFF (SEQ ID NO 1) of 1:500) were used in vivo for toxicological studies. Rats weighing about 250 g each were injected intravenously, via their tail vein, with increasing amounts of the SMOP starting from 100 μl and following an up-down protocol based on the outcome of the initial dose. The animals were observed for 2 weeks and were scored for any sign of immediate toxicity. SMOP did not cause immediate toxicity to the rats even at highest amount of administered (200 □L).

Particles in the size range of SMOPs are known to have high toxicity from animal studies because of self-aggregation and lung damage. SMOPs according to embodiments of the invention were found to be safe even in high doses tested in rats. Without being bound by theory, it is suggested that self-aggregation was not detected in SMOPs according to some embodiments of the invention because SMOPs were highly charged, thereby preventing self-aggregation.

EXAMPLE 2B

Macrophage Clearance of Aβ Bound by SMOP

As mentioned previously, AD and other diseases may be attributed to lack of clearance of Aβ0 and other amyloid-forming proteins, leading to amyloid buildup. Since the phagocytic pathway of Aβ has been hypothesized to be defective in AD, it was tested whether the KLVFF (SEQ ID NO 1)-modified SMOP are phagocytosed by the macrophagical/microglial cells through a non-Aβ-mediated pathway. The particle size and high charge density of the SMOP together with their proteinaceous structure may potentially make these particles highly susceptible to phagocytosis, even in patients with defective clearance of Aβ.

To induce optimal phagocytic activity, murine microglia (BV-2) cells were pre-stimulated with lipopolysaccharide (LPS) that generates inflammatory responses similar to those seen in AD patients. Phagocytotic activity was then studied by confocal microscopy as well as SEM. SMOPs were pre-loaded with Nile-red as a fluorescent probe to allow their identification within the cells. To ensure that the SMOPs localized to the intracellular space, the outer membrane and the nucleus of the live BV-2 cells were stained with Alexa-red wheat-germ agglutinin (WGA) and Hoechst dye, respectively. The stacked confocal images were then reconstructed to provide three-dimensional pictures of the cells. The images show that SMOPs with a diameter of about 0.7-1 μm were better phagocytosed by the BV-2 cells than SMOPs with larger diameter size. Further support for the phagocytosis of the SMOPs by BV-2 cells was provided by SEM analyses, which demonstrated the formation of hole-like structures (2.5-5 μm) on the membrane of the cells stimulated with LPS and incubated with the SMOPs. The holes most likely occurred on the cell membrane due to the disruption of the SMOPs inside the cells following the sample preparation and conditions under which SEM analyses were performed.

The uptake of the fluorescent microspheres by BV-2 cells was also confirmed by flow cytometry under conditions similar to those used for the microscopy studies. Cells were exposed for 2 hours to the Nile red-loaded KLVFF (SEQ ID NO 1)-modified SMOPs, washed and analyzed by FACS following detachment from plates. Fluorescent intensity of the cells increased upon incubation with the SMOPs, suggesting the phagocytosis of the particles by the cells. Moreover, pre-treatment of cells with LPS (1 microgram/ml (μg/ml)) for 4 h significantly enhanced the fluorescent intensity as compared to untreated cells. Assuming that microglia and macrophages in AD are exposed to inflammation conditions, these results suggest that SMOPs could clear Aβ in AD even while exposed to inflammation conditions.

To determine if the phagocytic pathway of the SMOPs is distinct from that of aggregated Aβ, BV-2 cells were incubated with pertussis toxin (PTX) and fucoidan as specific inhibitors of the G-protein receptor and the scavenger receptor, respectively, which have been shown to be essential for phagocytosis of Aβ. Previous studies have shown that inhibition of these receptors reduces the uptake of Aβ by macrophages. LPS-treated cells were incubated with PTX and fucoidan and then exposed for 30 minutes to aggregated FITC-Aβ or Nile-red-loaded KLVFF (SEQ ID NO 1)-modified SMOP. The extent of phagocytosed FITC-Aβ or KLVFF (SEQ ID NO 1)-modified SMOP was then compared by FACS for treated and non-treated cells. Treatment of BV-2 cells with either PTX or fucoidan reduced the uptake of the aggregated Aβ, as expected. However, these agents had a minimal effect on the phagocytosis of SMOPs, suggesting that the uptake mechanism of the SMOPs is distinct from that of Aβ, and may be effective in patients experiencing defective phagocytosis of Aβ.

EXAMPLE 2C

PEG-Modified SMOPs

SMOP modified by PEG and comprising a KLVFF (SEQ ID NO 1) Aβ-binding unit were synthesized as described in Example 1C. SEM showed that the SMOPs were spherical with relatively smooth surfaces. The average size of the SMOP was 373 nm which is smaller than the SMOPs without PEG modification. Confocal microscopy confirmed that the PEG-modified SMOPs encapsulated hydrophobic molecules, for example Nile-red, in their non-aqueous solvent-filled cores.

When tested in BV-2 cells, the rate of phagocytosis of PEG modified KLVFF (SEQ ID NO 1)-modified SMOPs reached a maximum later and the amount of phagocytosis increased relative to KLVFF (SEQ ID NO 1)-modified SMOPs without PEG.

Modification of SMOPs with PEG may further enhance the efficacy of SMOPs by allowing their enhanced time of vivo circulation and binding of amyloid to increase before undergoing phagocytosis by microglia or by macrophages.

EXAMPLE 2D

Additional Modifications of SMOPs to Enhance Biological Characteristics

In addition to modifications by PEG, SMOPs may also be modified by sugars to modify their biological characteristics. For example, SMOPs may be modified by mannose to modify their interaction with macrophages. Skirtenko et al describes methods of modifying mannose to form thiol-containing mannosyl derivatives. Such mannosyl derivatives may be added to reaction mixtures comprising proteins and sonicated according to embodiments of the invention to provide mannose substituted SMOPs. In addition to mannose, SMOPs may be modified with additional sugars such as glucose to provide enhanced biological characteristics.

EXAMPLE 3A

Additional Aβ-Binding Moieties Comprising Cyclic D,L-α-Peptides

Cyclic hexapeptides comprising alternating D- and L-amino acids were evaluated for their ability to bind Aβ and to prevent amyloid aggregation. The linear peptides were synthesized using solid-phase peptide synthesis using Fmoc methodology. Following synthesis, the linear peptides were cyclized on solid support.

Fmoc-L-Lys-ODmab. Fmoc-L-Lys(Boc)-OH was esterified by 4-{N-[1-(4,4-dimethyl-2,6-dioxocyclohexylidene)-3-methylbutyl]amino}benzyl ester (Dmab-OH) and treated with 50% TFA in $CH_2Cl_2$ to afford Fmoc-L-Lys-ODmab in 70% overall yield. The product was used for the peptide synthesis without further purification.

Synthesis of Cyclic D,L-α-Peptides. Cyclic D,L-α-peptides were synthesized on 2-Cl-trityl resin as follows. Fmoc-Lys-ODmab (0.78 g, 1 millimoles (mmol)) and DIEA (2 ml) in $CH_2Cl_2$ (8 ml) were added to 2-Cl-trityl chloride polystyrene resin (1 g, 1.6 mmol/gr) and the mixture was agitated for 4 hours. The resin was then washed with $CH_2Cl_2$ (3×) and MeOH and dried. The loading of the resin was then determined by quantification of Fmoc release following treatment of the resin with 20% piperidine in DMF. Peptides were then synthesized on an AAPPTec automated peptide synthesizer (Vantage) with HBTU/DIPEA mediated coupling reactions. Following completion of linear peptides, the resin was treated with 2% hydrazine hydrate in DMF to remove the Dmab protecting group. The resin was then washed with 5% DIEA in DMF and the linear peptide was cyclized, while still on resin, using a NMP solution of PyBOP, HOBT and DIEA (5, 5 and 15 eq.)) for 6 hours. The peptides were cleaved from the resin by treatment with a mixture of 95% TFA: 2.5% triisopropylsilane and 2.5% water for 2 hours. Crude peptides were then purified to homogeneity (>95% purity) by preparative RP-HPLC using a $C_{18}$ column, and identified by MALDI- or ESI-MS.

A ThT assay was performed as described previously at concentrations of 10 μM Aβ with a ratio of Aβ:cyclic D,L-α-peptide of either 1:1 or 1:1/3. Table 2 summarizes the structures of D,L-α-peptides tested as well as the reduction of amyloidogenic activity in percent at the concentrations tested. The cyclic peptides tested all consisted of 6 amino acids, in alternating D- and L-conformation. The sequences are described using single-letter amino acid code. Upper and lower case letters represent L- and D-amino acid residues, respectively. J and Z represent Norleucine and 2-aminooctanoic acid, respectively. Square brackets refer to cyclic peptides.

TABLE 2

| Sequence of cyclic peptide | Inhibition at 1:1 | Inhibition at 1:⅓ |
|---|---|---|
| [lLwHsK]: Cyclo-D-leucine-L-leucine-D-tryptophan-L-histidine-D-serine-L-lysine | 60 ± 7 | 32 ± 9 |
| [lLwHsA]: Cyclo-D-leucine-L-leucine-D-tryptophan-L-histidine-D-serine-L-alanine | 67 ± 5 | 48 ± 6 |
| [lLwHaK]: Cyclo-D-leucine-L-leucine-D-tryptophan-L-histidine-D-alanine-L-lysine | 56 ± 4 | 47 ± 10 |
| [lLwAsK]: Cyclo-D-leucine-L-leucine-D-tryptophan-L-alanine-D-serine-L-lysine | 73 ± 6 | 49 ± 8 |

TABLE 2-continued

| Sequence of cyclic peptide | Inhibition at 1:1 | Inhibition at 1:⅓ |
|---|---|---|
| [lLaHsK]: Cyclo-D-leucine-L-leucine-D-alanine-L-histidine-D-serine-L-lysine | 4 ± 4 | 5 ± 4 |
| [lAwHsK]: Cyclo-D-leucine-L-alanine-D-tryptophan-L-histidine-D-serine-L-lysine | 44 ± 9 | 3 ± 10 |
| [aLwHsK]: Cyclo-D-alanine-L-leucine-D-tryptophan-L-histidine-D-serine-L-lysine | 53 ± 12 | 12 ± 12 |
| [lJwHsK]: Cyclo-D-leucine-L-noreucine-D-tryptophan-L-histidine-D-serine-L-lysine | 69 ± 5 | 37 ± 10 |
| [lZwHsK]: Cyclo-D-leucine-L-2-aminooctanoic acid-D-tryptophan-L-histidine-D-serine-L-lysine | 55 ± 14 | 42 ± 6 |

As seen in the table above, cyclic D,L-α-peptides had an anti-amyloid aggregation effect. The cyclic peptide (designated cyclic peptide-2) having the sequence [1JwHsK], had a drastic effect on amyloid aggregation. However, the linear equivalent of cyclic peptide-2 did not inhibit amyloid formation. Cyclic peptide 2 was also effective in reducing Aβ-induced toxicity in PC12 cells.

According to embodiments of the invention, cyclic peptides may comprise between 6 or 8 amino acids. According to an embodiment, the cyclic peptide comprises 6 amino acids. In an embodiment, half of the amino acid residues are in the D-formation, and the other half are in the L-formation. In an embodiment of the invention, the amino acids alternate between the D and L-formations.

Without being bound by theory, it is suggested that cyclic peptides associate with Aβ via hydrogen bonding, π-π and hydrophobic interactions. They then induce conformational changes to the structure of Aβ, thereby inhibiting aggregation and/or fibril formation. The inventors suggest that the cyclic D,L-α-peptides induce a parallel β-sheet structure in Aβ (as opposed to toxic anti-parallel conformation of aggregated Aβ) and alter its oligomer distribution by stabilizing low-molecular-weight species.

Cyclic D,L-α-peptides may be used as independent agents for treatment and/or diagnosis of amyloid-associated diseases according to embodiments of the invention. In addition, cyclic D,L-α-peptides may be modified to comprise at least one thiol group without altering their biological activity and may be conjugated to proteinaceous particles to form SMOPs via methods described herein including sonication. Such cyclic D,L-α-peptide-modified SMOPs may be used for treatment or diagnosis of diseases associated with amyloid accumulation.

EXAMPLE 3B

Additional Aβ-Binding Moieties

Various agents have been found to inhibit amyloid fibril formation. SMOPs according to embodiments of the invention may be prepared using various amyloid-binding agents. Examples of such amyloid-binding agents include scy6llo-cyclohexanehexyl, tramiprosate, 2-Hydroxy-3-ethoxy-benzaldehyde and phenol red. These agents can be modified by a thiol group and sonicated with a protein in order to form SMOPs according to embodiments of the invention.

Polyphenols are a class of compounds which may be used to form amyloid-binding SMOPs according to an embodiment of the invention. Examples of such polyphenols include: Nordihydroguaiaretic acid, curcumin, dobutamine, rosmarinic acid, congo red, 3,3'-bis(3-hydroxyphenyl) pyridazine-3,6-diamine, resveratrol, myricetin, morin, quercetin, kaempferol, apomorphine, exifone, 2,2'-dihydroxybenzophenon, 2,3,4,2',4'-pentahydroxybenzophenone, baicalein, apigenin, catechin, epicatechin, phenolsulphonaphthalein, epicatechin gallate, epigallocatechin gallate, hypericin and tannic acid. These agents can be modified by a thiol group and sonicated with a protein in order to form SMOPs according to embodiments of the invention Short peptide inhibitors of amyloid aggregation as described in Neddenriep et al, may be used to form SMOPs according to embodiments of the invention.

As to amino acid sequences, including peptides derived from the Aβ sequence, one of skill will recognize that individual substitutions, deletions or additions to a nucleic acid, peptide, polypeptide, or protein sequence which alters, adds or deletes a single amino acid or a small percentage of amino acids in the encoded sequence is a "substantially identical derivative" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M)

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, optionally about 65%, about 70%, about 75%, about 80%, about 85%, about 90%, or about 95% identity over a specified region), when compared and aligned for maximum correspondence over a comparison window, or designated region as measured using one of the following sequence comparison algorithms or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence or a polynucleotide or polypeptide.

EXAMPLE 4

Administration of SMOP to Humans for Treatment of Disease

SMOP according to embodiments of the invention may be combined with a pharmaceutically acceptable excipient and administered to a patient in need of amyloid modifying treatment. In an embodiment, the patient suffers from a disease associated with amyloid formation selected from the group consisting of Alzheimer's disease, Lewy body dementia, cerebral amyloid angiopathy and inclusion body myositis. In an embodiment, the patient suffers from a disease selected from the group consisting of Diabetes mellitus type 2, Parkinson's disease, transmissible spongiform encephalopathy, Huntington's disease, medullary carcinoma of the thyroid, isolated atrial amyloidosis, atherosclerosis, rheumatoid arthritis, prolactinomas, familial amyloid polyneuropathy, amyloidosis, lattice corneal dystrophy, systemic AL amyloidosis and inclusion body myositis.

Of the mentioned diseases associated with amyloid formation, different types of amyloids are involved in the pathology of the disease. In an embodiment of the invention, methods of treatment using specific amyloid-binding moieties are conjugated to SMOPs for treatment of specific diseases associated with specific amyloids.

In an embodiment, a pharmaceutical composition is provided comprising a plurality of SMOP particles and at least one pharmaceutically acceptable excipient.

In an embodiment of the invention, provided is a method for treating a patient, the method comprising parenteral administration of a pharmaceutical composition, comprising a plurality of SMOP particles. In an embodiment, the parenteral administration is through the intravenous, subcutaneous or intramuscular route.

In an embodiment, the amount of SMOP administered to the patient ranges from 0.01 mg per day to about 1 g per day. In an embodiment, the treatment is administered between 1 and 4 times daily. In an embodiment, the treatment is administered once weekly, or once a month.

EXAMPLE 5

Administration of SMOP to Humans for Diagnosis of Disease

In order to diagnose a patient to determine if he or she suffers from a disease associated with amyloid aggregation, SMOPs according to embodiments of the invention may be used. In an embodiment, an SMOP comprising a contrasting agent is administered. In an embodiment, the contrasting agent is dissolved within a non-aqueous layer of solvent enclosed by the protein layer of the SMOP. In an embodiment, the contrasting agent is chemically bound to the surface of the SMOP by binding to a protein or to an Aβ binding moiety.

In an embodiment of the invention, a method of diagnosis of a patient is provided comprising administering to a patient an SMOP comprising an Aβ binding moiety and at least one contrasting agent; subjecting the patient to a diagnostic test to determine presence of an amyloid plaque; and treating the patient with a treatment to treat a disease associated with an amyloid plaque. An exemplary contrasting agent which may be used is magnetite. SMOPs may be manufactured with magnetite in an oil layer, surrounded by a protein, and may be administered to allow binding of an amyloid plaque. A patient may then undergo magnetic resonance imaging (MRI) diagnosis to assess for quantities and locations of magnetite, thereby indicating presence and locations of amyloid plaques.

In addition, other diagnostic agents such as radioactive agents may be used for diagnosis. For example, radioactive Technetium-99 ($^{99}Tc$) may be incorporated into SMOP according to embodiments of the invention. The SMOPs may then be administered and the patient may undergo computed tomography (CT) scanning to locate potential amyloid plaques.

EXAMPLE 6

Synthetic Procedures for Manufacture of SMOP

In addition to manufacturing SMOPs modified by Aβ-binding moieties, additional embodiments of the invention relate to manufacturing SMOPs modified (on their outer surfaces) by other biologically active components, such as peptides.

Methods according to embodiments of the invention comprise sonicating mixtures of thiol-containing proteins and biologically active components to form SMOPs modified by biologically active components. In an embodiment of the invention, the mixtures further comprise an organic solvent. In an embodiment of the invention, the organic solvent is an oil. In an embodiment, the organic solvent is n-dodecane. In an embodiment, the mixture further comprises a fluorescent agent. In an embodiment, the fluorescent agent comprises curcumin or Nile red.

In an embodiment of the invention, SMOP further comprises a contrasting agent. SMOPs comprising, for example a metal-comprising contrasting agent such as magnetite, may be detectable via MRI. SMOPs comprising magnetite may be synthesized by addition of iron pentacarbonyl to the reaction mixture to form magnetite-comprising SMOPs. In addition, magnetite may be added to the reaction solution and incorporated into the microspheres.

In an embodiment, the oil is a pharmaceutically acceptable oil. In an embodiment, the pharmaceutically acceptable oil is selected from the group consisting of: a naturally-derived liquid oil, such as canola oil, corn oil, coconut oil, sunflower seed oil, vegetable oil, cottonseed oil, mineral oil, peanut oil, sesame oil, soybean oil, and/or olive oil.

In an embodiment, the ratio of thiol containing protein to biologically active peptide in the reaction mixture is 1:1 to 1:1000.

In an embodiment the acoustic power applied to the reaction mixture is between 100 and 500 W/cm$^2$. In an embodiment, the acoustic power is about 150 W/cm$^2$.

In an embodiment, the mixture is sonicated for between about 1 and about 30 minutes. In an embodiment the mixture is sonicated for about 3 minutes.

In an embodiment, the reaction provides particles having an average particle size, as determined by DLS, between about 0.2 and about 2 µm. In an embodiment, the average particle size is between about 0.4 and about 1 µm. In an embodiment, the average particle size is between about 0.7 and about 1 µm.

There is further provided in accordance with an embodiment of the invention, a particle comprising: a spherical protein layer comprising a protein, a polypeptide, a biopolymer or a polymer, and an amyloid-binding moiety conjugated to the protein layer. Optionally, the diameter of the particle is between about 0.2 and about 2 µm, between about 0.4 and about 1 µm, between about 0.7 to about 1 µm. Optionally, the amyloid-binding moiety is a peptide which optionally binds Aβ. Optionally, the peptide is derived from Aβ. Optionally, the peptide comprises the amino acid sequence KLVFF (SEQ ID NO 1). Optionally, the amyloid-binding moiety comprises a cyclic peptide having an even number of amino acids. Optionally, the cyclic peptide comprises 6 or 8 amino acids, optionally alternating L- and D-amino acids. Optionally, the cyclic peptide is composed of 6 amino acids, 3 of the amino acids in L-configuration and 3 of the amino acids in D-configuration. Optionally, the cyclic peptide is selected from the group consisting of cyclic peptides having the sequence: D-leucine-L-leucine-D-tryptophan-L-histidine-D-serine-L-lysine; D-leucine-L-leucine-D-tryptophan-L-histidine-D-serine-L-alanine; D-leucine-L-leucine-D-tryptophan-L-histidine-D-alanine-L-lysine; D-leucine-L-leucine-D-tryptophan-L-alanine-D-serine-L-lysine; D-leucine-L-leucine-D-alanine-L-histidine-D-serine-L-lysine; D-leucine-L-alanine-D-tryptophan-L-histidine-D-serine-L-lysine; D-alanine-L-leucine-D-tryptophan-L-histidine-D-serine-L-lysine; D-leucine-L-noreucine-D-tryptophan-L-histidine-D-serine-L-lysine and D-leucine-L-2-aminooctanoic acid -D-tryptophan-L-histidine-D-serine-L-lysine. Optionally, the amyloid-binding moiety is bound to the protein through a disulfide bond. Optionally, the protein comprises an albumin protein. Optionally, the protein comprises human serum albumin or BSA. Optionally, the particle comprises an inner solvent layer, surrounded by the protein layer. Optionally, the solvent layer comprises an oil, optionally a pharmaceutically acceptable oil, optionally, canola oil. Optionally, the particle further comprising PEG attached to the surface of a particle. Optionally, the particle comprises a contrasting agent.

There is further provided in accordance with an embodiment of the invention, a method for the manufacture of a surface modified proteinaceous particle comprising: combining a biologically active moiety having a thiol group and a protein having a thiol group with an organic solvent to form a reaction mixture, and sonicating the reaction mixture to form a surface modified proteinaceous particle. Optionally, the organic solvent is pharmaceutically acceptable oil. Optionally, the method further comprises separating the surface modified proteinaceous particle from the reaction mixture. Optionally, the surface modified proteinaceous particle is formed from the protein and the biologically active moiety in a one-pot reaction. Optionally, the biologically active moiety comprises an amyloid-binding moiety. Optionally, the protein comprises an albumin. Optionally, the reaction mixture further comprises a contrasting agent.

There is further provided in accordance with an embodiment of the invention, a cyclic peptide having the sequence selected from the group consisting of: Cyclo-D-leucine-L-leucine-D-tryptophan-L-histidine-D-serine-L-lysine; Cyclo-D-leucine-L-leucine-D-tryptophan-L-histidine-D-serine-L-alanine; Cyclo-D-leucine-L-leucine-D-tryptophan-L-histidine-D-alanine-L-lysine; D-leucine-L-leucine-D-tryptophan-L-alanine-D-serine-L-lysine; Cyclo-D-leucine-L-leucine-D-alanine-L-histidine-D-serine-L-lysine; Cyclo-D-leucine-L-alanine-D-tryptophan-L-histidine-D-serine-L-lysine; Cyclo-D-alanine-L-leucine-D-tryptophan-L-histidine-D-serine-L-lysine; Cyclo-D-leucine-L-noreucine-D-tryptophan-L-histidine-D-serine-L-lysine and Cyclo-D-leucine-L-2-aminooctanoic acid-D-tryptophan-L-histidine-D-serine-L-lysine.

There is further provided in accordance with an embodiment of the invention, a pharmaceutical composition for treatment or diagnosis of a disease comprising a plurality of particles according to embodiments of the invention. Optionally, the average diameter of the plurality of particles is between about 0.2 and about 2 µm, between about 0.4 and about 1 µm or between about 0.7 to about 1 µm.

There is further provided in accordance with an embodiment of the invention, a method of treating a disease associated with amyloid formation comprising administering to a patient in need thereof a pharmaceutical composition according to an embodiment of the invention. Optionally, the disease is selected from the group consisting Alzheimer's disease, Lewy body dementia, cerebral amyloid angiopathy and inclusion body myositis, diabetes mellitus type 2, Parkinson's disease, transmissible spongiform encephalopathy, Huntington's disease, medullary carcinoma of the thyroid, isolated atrial amyloidosis, atherosclerosis, rheumatoid arthritis, prolactinomas, familial amyloid polyneuropathy, amyloidosis, lattice corneal dystrophy, systemic AL amyloidosis and inclusion body myositis.

There is further provided in accordance with an embodiment of the invention, a method for treating a disease associated with amyloid formation comprising: administering to a patient a particle according to an embodiment of the invention, analyzing the patient to determine presence of particles associated with amyloid in the patient and determining if the patient has a disease and treating the patient if the patient was determined to have a disease associated with amyloid. Optionally, the disease is selected from the group consisting of Alzheimer's disease, Lewy body dementia, cerebral amyloid angiopathy and inclusion body myositis, diabetes mellitus type 2, Parkinson's disease, transmissible spongiform encephalopathy, Huntington's disease, medullary carcinoma of the thyroid, isolated atrial amyloidosis, atherosclerosis, rheumatoid arthritis, prolactinomas, familial amyloid polyneuropathy, amyloidosis, lattice corneal dystrophy, systemic AL amyloidosis and inclusion body myositis.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

WORKS CITED

A. J. Doig. *Current Opinion in Drug Discovery & Development* 2007, 10, 533-539.

M. J. Kogan, N. G. Bastus, R. Amigo, D. Grillo-Bosch, E. Araya, A. Turiel, A. Labarta, E. Giralt and V. F. Puntes. *Nano Letters* 2006, 6, 110-115.

B. Neddenriep, A. Calciano, D. Conti, E. Sauve, M. Paterson, E. Bruno and D. A. Moffet. *The Open Biotechnology Journal,* 2011, 5, 39-46.

N. Skiertenko, M. Richman, Y. Nitzan, A. Gedanken and S Rahimipour. *Chem. Commun.,* 2011, 47, 12277-12279.

---

The invention claimed is:

1. A cyclic peptide having the sequence selected from the group consisting of:

Cyclo-D-leucine-L-leucine-D-tryptophan-L-histidine-D-serine-L-alanine;

Cyclo-D-leucine-L-leucine-D-tryptophan-L-histidine-D-alanine-L-lysine;

Cyclo-D-leucine-L-leucine-D-tryptophan-L-alanine-D-serine-L-lysine;

Cyclo-D-leucine-L-leucine-D-alanine-L-histidine-D-serine-L-lysine;

Cyclo-D-leucine-L-alanine-D-tryptophan-L-histidine-D-serine-L-lysine; and

Cyclo-D-leucine-L-2-aminooctanoic acid -D-tryptophan-L-histidine-D-serine-L-lysine.

* * * * *

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: Beta Amyloid binding moiety

<400> SEQUENCE: 1

Lys Leu Val Phe Phe
1               5

<210> SEQ ID NO 2
<211> LENGTH: 5
<212> TYPE: PRT
<213> ORGANISM: Artificial Sequence
<220> FEATURE:
<223> OTHER INFORMATION: Beta Amyloid binding moiety
<220> FEATURE:
<221> NAME/KEY: VARIANT
<222> LOCATION: (5)..(5)
<223> OTHER INFORMATION: C-terminal Amidation

<400> SEQUENCE: 2

Lys Leu Val Phe Phe
1               5

<210> SEQ ID NO 3
<211> LENGTH: 6
<212> TYPE: PRT
<213> ORGANISM: Artificial Sequence
<220> FEATURE:
<223> OTHER INFORMATION: Beta amyloid binding moiety
<220> FEATURE:
<221> NAME/KEY: VARIANT
<222> LOCATION: (6)..(6)
<223> OTHER INFORMATION: C-Terminal Amidation

<400> SEQUENCE: 3
```

```
Lys Leu Val Phe Phe Cys
1               5

<210> SEQ ID NO 4
<211> LENGTH: 6
<212> TYPE: PRT
<213> ORGANISM: Artificial Sequence
<220> FEATURE:
<223> OTHER INFORMATION: Scrambled peptide control
<220> FEATURE:
<221> NAME/KEY: VARIANT
<222> LOCATION: (6)..(6)
<223> OTHER INFORMATION: C-Terminal Amidation

<400> SEQUENCE: 4

Phe Val Lys Leu Phe Cys
1               5
```